(12) United States Patent
Cambron et al.

(10) Patent No.: US 8,569,691 B2
(45) Date of Patent: Oct. 29, 2013

(54) PRECONCENTRATOR FOR ANALYSIS INSTRUMENTS

(75) Inventors: Scott Cambron, Louisville, KY (US); Thomas J. Roussel, Louisville, KY (US); Robert S. Keynton, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 219 days.

(21) Appl. No.: 12/953,108

(22) Filed: Nov. 23, 2010

(65) Prior Publication Data
US 2012/0132798 A1    May 31, 2012

Related U.S. Application Data

(60) Provisional application No. 61/264,047, filed on Nov. 24, 2009.

(51) Int. Cl.
*H01J 49/26* (2006.01)
(52) U.S. Cl.
USPC .......................... 250/288; 250/281; 250/282
(58) Field of Classification Search
USPC ........................................ 250/281, 282, 288
See application file for complete search history.

(56) References Cited

U.S. PATENT DOCUMENTS

| | | |
|---|---|---|
| 3,768,300 A | 10/1973 | Nemeth |
| 4,011,301 A | 3/1977 | Young |
| 4,698,071 A | 10/1987 | Elias |
| 4,805,441 A | 2/1989 | Sides et al. |
| 4,839,143 A | 6/1989 | Vora et al. |
| 4,935,040 A | 6/1990 | Goedert |
| 4,964,309 A | 10/1990 | Jenkins |
| 5,014,541 A | 5/1991 | Sides et al. |
| 5,035,776 A | 7/1991 | Knapp et al. |
| 5,053,343 A | 10/1991 | Vora et al. |
| 5,083,019 A | 1/1992 | Spangler |

(Continued)

FOREIGN PATENT DOCUMENTS

| | | |
|---|---|---|
| DE | 19851821 A1 | 5/2000 |
| EP | 0649337 B1 | 9/1996 |

(Continued)

OTHER PUBLICATIONS

U.S. Appl. No. 11/881,333, filed Jul. 25, 2007, Martin.

(Continued)

*Primary Examiner* — Nicole Ippolito
(74) *Attorney, Agent, or Firm* — Wyatt, Tarrant & Combs, LLP; Stephen C. Hall

(57) ABSTRACT

An interchangeable preconcentrator assembly for delivering an analyte to an analysis instrument. The assembly includes a housing defining an inner chamber. An inlet is in fluid communication with the inner chamber, an outlet is in fluid communication with the inner chamber for delivering fluid to the inlet of the analysis instrument, and an exhaust outlet is in fluid communication with the inner chamber. A plurality of removable preconcentrator packages are disposed within the inner chamber. Each of the removable preconcentrator packages including a microscale preconcentrator. A fluid flow path is defined between the inlet and the inner chamber. A first fluid flow path is defined between the preconcentrators and the exhaust outlet, and a second fluid flow path is defined between the preconcentrators and the outlet. A selectably operable valve directs fluid flow from the inner chamber into either the first fluid flow path or the second fluid flow path.

20 Claims, 10 Drawing Sheets

(56) References Cited

U.S. PATENT DOCUMENTS

| | | | |
|---|---|---|---|
| 5,092,155 | A | 3/1992 | Rounbehler et al. |
| 5,092,218 | A | 3/1992 | Fine et al. |
| 5,142,143 | A | 8/1992 | Fite et al. |
| 5,395,589 | A | 3/1995 | Nacson |
| 5,465,607 | A * | 11/1995 | Corrigan et al. ............ 73/23.36 |
| 5,578,271 | A | 11/1996 | Simon et al. |
| 5,690,763 | A | 11/1997 | Ashmead et al. |
| 5,707,502 | A | 1/1998 | McCaffrey et al. |
| 5,720,798 | A | 2/1998 | Nickerson et al. |
| 5,753,832 | A | 5/1998 | Bromberg et al. |
| 5,792,423 | A | 8/1998 | Markelov |
| 5,817,012 | A | 10/1998 | Schoendorfer |
| 5,847,291 | A | 12/1998 | Green et al. |
| 5,854,431 | A | 12/1998 | Linker |
| 5,932,482 | A | 8/1999 | Markelov |
| 5,970,803 | A | 10/1999 | Staples et al. |
| 6,001,308 | A | 12/1999 | Marlow et al. |
| 6,022,748 | A | 2/2000 | Charych et al. |
| 6,057,162 | A | 5/2000 | Rounbehler et al. |
| 6,066,295 | A | 5/2000 | Bernstein et al. |
| 6,085,601 | A | 7/2000 | Linker |
| 6,087,183 | A | 7/2000 | Zaromb |
| 6,171,378 | B1 | 1/2001 | Manginell et al. |
| 6,239,428 | B1 | 5/2001 | Kunz |
| 6,242,195 | B1 | 6/2001 | Idusogie et al. |
| 6,257,835 | B1 | 7/2001 | Kaehler |
| 6,295,860 | B1 | 10/2001 | Sakairi et al. |
| 6,316,268 | B1 | 11/2001 | Yang |
| 6,326,615 | B1 | 12/2001 | Syage et al. |
| 6,345,545 | B1 | 2/2002 | Linker et al. |
| 6,354,160 | B1 | 3/2002 | Staples et al. |
| 6,442,997 | B1 | 9/2002 | Megerle |
| 6,485,987 | B1 | 11/2002 | Charych et al. |
| 6,527,835 | B1 | 3/2003 | Manginell et al. |
| 6,619,143 | B2 | 9/2003 | Danylewych-May et al. |
| 6,666,907 | B1 | 12/2003 | Manginell et al. |
| 6,706,091 | B1 | 3/2004 | Robinson et al. |
| 6,759,013 | B2 | 7/2004 | Kaltenbach et al. |
| 6,811,587 | B1 | 11/2004 | Lorey |
| 6,869,501 | B2 | 3/2005 | Davidson et al. |
| 6,893,879 | B2 | 5/2005 | Petersen et al. |
| 6,914,220 | B2 | 7/2005 | Tian et al. |
| RE38,797 | E | 9/2005 | Linker |
| 6,989,891 | B2 | 1/2006 | Braig |
| 7,104,112 | B2 | 9/2006 | Bonne |
| 7,118,712 | B1 | 10/2006 | Manginell et al. |
| 7,141,786 | B2 | 11/2006 | McGann et al. |
| 7,244,288 | B2 | 7/2007 | Belyakov |
| 7,273,517 | B1 | 9/2007 | Lewis et al. |
| 7,306,649 | B2 | 12/2007 | Boyle |
| 2002/0055184 | A1 | 5/2002 | Naylor et al. |
| 2003/0106799 | A1 | 6/2003 | Covington et al. |
| 2004/0035226 | A1 | 2/2004 | Allen et al. |
| 2004/0035227 | A1 | 2/2004 | Allen et al. |
| 2004/0060346 | A1 | 4/2004 | Bonne et al. |
| 2005/0014134 | A1 | 1/2005 | West |
| 2005/0095722 | A1 | 5/2005 | McGill et al. |
| 2005/0226778 | A1 | 10/2005 | Houser et al. |
| 2005/0253061 | A1 | 11/2005 | Cameron et al. |
| 2006/0257287 | A1 | 11/2006 | Call |
| 2007/0084347 | A1 | 4/2007 | Boyle et al. |
| 2007/0176092 | A1 | 8/2007 | Miller et al. |
| 2009/0028208 | A1 | 1/2009 | Martin |
| 2009/0090197 | A1 | 4/2009 | Finlay |
| 2010/0236341 | A1 * | 9/2010 | Martin et al. ............ 73/863.12 |

FOREIGN PATENT DOCUMENTS

| | | |
|---|---|---|
| EP | 0502998 B1 | 7/1999 |
| GB | 2243917 A | 11/1991 |
| WO | WO 9735174 A1 | 9/1997 |
| WO | 0140793 | 6/2001 |
| WO | WO 2004052540 A2 | 6/2004 |
| WO | WO 2004083806 A2 | 9/2004 |
| WO | WO 2005029030 A2 | 3/2005 |
| WO | 2006003646 A2 | 1/2006 |
| WO | 2006003646 A3 | 1/2006 |
| WO | WO 2006013396 A2 | 2/2006 |
| WO | WO 2006046077 A1 | 5/2006 |
| WO | WO 2006046988 A1 | 5/2006 |
| WO | WO 2006073434 A2 | 7/2006 |
| WO | WO 2006073440 A2 | 7/2006 |
| WO | WO 2006104603 A2 | 10/2006 |
| WO | WO 2007041551 A2 | 4/2007 |
| WO | WO 2007044473 A2 | 4/2007 |
| WO | WO 2007056488 A1 | 5/2007 |

OTHER PUBLICATIONS

U.S. Appl. No. 11/542,453, filed Oct. 2, 2006, McGill et al.

U.S. Appl. No. 10/865,685, filed Jun. 10, 2004, McGill et al.

U.S. Appl. No. 12/337,449, filed Dec. 17, 2004, Cambron et al.

Berger, T., et al., "Development of Electrochemical Sensors for Trace Detection of Explosives and for the Detection of Chemical Warfare Agents", Proceedings of the SPIE—The International Society for Optical Engineering, vol. 4038, pp. 452-461, 2000.

Cabalo, J., et al., "Trace Detection of Explosives with Low Vapor Emissions by Laser Surface Photofragmentation-Fragment Detection Spectroscopy with an Improved Ionization Probe", Applied Optics, vol. 44, No. 6, pp. 1084-1091, Feb. 20, 2005.

Da Silva, J. A. F., et al., Simulations of silicon microstructure for preconcentration of metallic ions, Microelectronics Technology and Devices. SBMICRO 2003. Proceedings of the Eighteenth International Symposium, Sep. 2003, pp. 420-427, Pennington, NJ, USA.

Davidson, William R., et al., "Vapor and Particle Sampling in the Detection of Terrorists Explosives", Proc. 50$^{th}$ ASMS Conf. Mass Spectrom. Allied Top., pp. 697-698, 2002.

Ewing, R. G., et al., "Detection of Volatile Vapours Emitted from Explosives with a Handheld Ion-Mobility Spectrometer", Field Analytical Chemistry and Technology, vol. 5, No. 5, pp. 215-221, 2001.

Fisher, M., et al., "Explosive Detection Using High-Volume Vapor Sampling and Analysis by Trained Canines and Ultra-Trace Detection Equipment", Proceedings of the SPIE—The International Society for Optical Engineering, vol. 5403, No. 1, pp. 409-417, Apr. 12-16, 2004.

Goeringer, Douglas, et al., "Comparison of Atmospheric Pressure Chemical Ionization and Atmospheric Sampling Glow Discharge Ionization Combined with Tandem Mass Spectrometry for Explosives Vapor Detection", Proc. 50th ASMS Conf. Mass Spectrom. Allied Top., pp. 707-708, 2002.

Hannum, David W., et al., "Miniaturized Explosive Preconcentrator for Use in a Man-Portable Field Detection System", International Nuclear Materials Management Conference, Phoenix, AZ, Aug. 2, 1999.

Ho, C.K., et al., "Integrated Chemiresistor Sensors with Preconcentrators for Monitoring Volatile Organic Compounds in Water", Proceedings of the 2005 World Water and Environmental Resources Congress. EWRI 2005: Impacts of Global Climate Change, Anchorage, Alaska, May 15, 2005.

Holland, R.M., et al., "Handheld GC instrumentation for Chemical Weapons Convention treaty verification inspections Monograph Title—Field screening methods for hazardous wastes and toxic chemicals. VIP-47, vol. 1", Air and Waste Management Association, Pittsburgh, PA, 1995.

Hughes, David, "Explosive Detection Equipment Firms Develop Enhanced X-Ray and Vapor Technologies", Aviation Week & Space Technology, vol. 134, No. 12, pp. 60-62, Mar. 25, 1991.

Hughes, R. C., et al., "Chemical sensing with an integrated preconcentrator/chemiresistor array", Chemical and Biological Sensors and Analytical Methods II Proceedings of the International Sympoium, 2001, pp. 348-354, Electrochemical Society, Pennington, NJ, USA.

Hughes, R.C., et al., "A MEMS Based Hybrid Preconcentrator/Chemiresistor Chemical Sensor," Sep. 1, 2002.

Lucero, Daniel P., "User Requirements and Performance Specifications for Explosive Vapor Detection Systems", Journal of Testing & Evaluation, vol. 13, No. 3, pp. 222-233, 1985.

(56) References Cited

OTHER PUBLICATIONS

Martin, Michael, et al., "Characterization of a Cascaded Micro-Preconcentrator Sampler for IMS", International Symposium in Thun, Switzerland on Jul. 25-31, 2009.

Martin, Michael, et al., "Microfabricated vapor preconcentrator for portable ion mobility spectroscopy", Sensors and Actuators, B: Chemical, vol. 126, No. 2, Oct. 1, 2007.

McGill, R. A., et al., "A micromachined preconcentrator for enhanced trace detection of illicit materials, 2003 International Semiconductor Device Research Symposium", IEEE, Piscataway, NJ, USA.

McGill, R. A., et al., "Choosing polymer coatings for chemical sensors", American Chemical Society, Chemtech, Sep. 1994.

Owano, T. G., et al., "Ultrasensitive Detection of Explosives Vapor Using Mid-IR Cavity Ring-Down Spectroscopy", Technical Digest. Summaries of papers presented at the Conference on Lasers and Electro-Optics, Postconference Technical Digest, pp. 519-520, 2001.

Parmeter, J.E., et al., "Development of a portable preconcentrator/ion mobility spectrometer system for the trace detection of narcotics", Sandia National Labs. Report, Albuquerque, NM, Aug. 1997.

Parmeter, J.E., et al., "Explosives detection portal for high-volume personnel screening", Proceedings of the 1998 Enforcement and Security Technologies, Boston, MA, 1999.

Parmeter, John, et al "Overview of Explosives Detection Research and Development in Department 5848 at Sandia National Laboratories", 16th Annual NDIA Security Technology Symposium & Exhibition, Jun. 26-29, 2000.

Ritchie, Robert K., et al., "Detection of Explosives, Narcotics, and Taggant Vapors by an Ion Mobility Spectrometry Particle Detector", Proceedings of the SPIE—The International Society for Optical Engineering, vol. 2092, pp. 87-93, 1994.

Rodacy, Philip J., et al., "Unexploded ordnance classification sensor for underwater applications", Sandia National Labs. Report, Albuquerque, NM, Apr. 1, 2000.

Rhykerd, C., et al., "Airport testing an explosives detection portal", Institute of Nuclear Materials Management (INMM) annual meeting, Naples, FL, Jul. 26-30, 1998.

Sandia National Laboratories, "Micro Analytical Systems Department Technology—µChemLab, Fact Sheet", Dec. 30, 2002.

Seman, G., et al., "Detection of Hidden Explosives on Passenger Aircraft Using Hand Searches, Bio-Sensors and Vapour Detectors", Proceedings of the 1977 International Conference on Crime Countermeasures—Science and Engineering, pp. 65-84, 1977.

Sigman, M. E., et al., "Performance Evaluation of an In-Injection Port Thermal Desorption/Gas-Chromatographic/Negative Ion Chemical Ionization Mass Spectrometric Method for Trace Explosive Vapour Analysis", Analytical Chemistry, vol. 73, No. 4, pp. 792-798, Feb. 15, 2001.

Simoes, E.W., et al., "Study of preconcentration of non-polar compounds in microchannels with constrictions", Sensors and Actuators, vol. 115, No. 1, Lausanne, Switzerland, May 23, 2006, pp. 232-239.

Spicer, James B., et al., "Overview: MURI Center on Spectroscopic and Time Domain Detection of Trace Explosives in Condensed and Vapor Phases", Proc. SPIE Int Soc Opt Eng., vol. 5089, No. 2, pp. 1088-1094, 2003.

Staples, Edward J., et al., "Ultrahigh-Speed Chromatography and Virtual Chemical Sensors for Detecting Explosive and Chemical Warfare Agents", IEEE Sensors J., vol. 5, No. 4, pp. 622-631, Aug. 2005.

Voiculescu, I., et al., "Micropreconcentrator for Enhanced Trace Detection of Explosives and Chemical Agents", IEEE Sensors Journal, vol. 6, No. 5, pp. 1094-1104, Oct. 2006.

"Smiths Detection Introduces Next-Generation Handheld Detector for Narcotics, Explosives, Chemical Warfare Agents and Toxic Industrial Chemicals", Smiths Detection, Pine Brook, NJ, Jun. 3, 2004.

"Technest Provides Status Update on Remote Standoff Chemical Agent and Explosives Detection Sensor Development Program", Technest Holdings Inc., Boston, MA, Jan. 16, 2006.

European Patent Office; European Search Report; Aug. 28, 2013; pp. 1-7; European Patent Office; the Netherlands.

\* cited by examiner

PRECONCENTRATOR FOR ANALYSIS INSTRUMENTS

PRIORITY CLAIM AND REFERENCE TO RELATED APPLICATION

This application claims the benefit of U.S. Provisional Application Ser. No. 61/264,047, filed Nov. 24, 2009, under 35 U.S.C. §119.

STATEMENT OF GOVERNMENT INTEREST

This invention was made with Government assistance under Grant No. 2004-IJ-CX-K0555 issued by Department of Justice. The Government has certain rights in the invention.

FIELD OF THE INVENTION

The invention relates generally to devices and methods for analyte detection. A more particular field of the invention is analyte collection.

BACKGROUND OF THE INVENTION

Analyte detection is becoming increasingly important as a security and safety measure. Transportation, commercial, government, educational, and other facilities have a need for the sensitive and rapid detection of analytes, including those that are indicative of explosives or other substances that pose a threat. In addition, in industrial, residential, and commercial settings, analyte detection can provide warning of particles that pose a health or safety risk. Example analytes to be detected include, as nonlimiting examples, hazardous materials, including explosive-related materials, toxic industrial chemicals (TICS), narcotics, and chemical or biological agents, though other analytes may also be detected.

Analysis instruments, such as but not limited to detectors, have been developed and remain under development for detection of analytes. A nonlimiting example analysis instrument currently used in portable and larger forms is the Ion Mobility Spectrometer (IMS), such as the GE VaporTrace models. A typical IMS device has separate particle and vapor modes. In particle mode, an assembly is affixed to the device to accept and desorb particles from a substrate such as a swab during baggage screening. The swab is inserted into the assembly and is heated to desorb any collected particulates, and the particulates are directed via vacuum into the instrument for analysis. This assembly or a different assembly can be affixed to the device for vapor mode, in which the device collects vapors for analyte detection. As one nonlimiting example application, vapor mode is often used to sample contained areas such as automobile trunks at the entrances to military facilities.

Speed and sensitivity are primary concerns for researchers and manufacturers when using analysis instruments, and devices such as preconcentrators can provide improvements for both. Preconcentrators offer the opportunity to enhance the performance of any type of analysis instrument by increasing the concentration of analyte in a volume of fluid sent for analysis. Generally, preconcentrators collect analyte over a period of time during absorption, and then provide a concentrated fluid stream to the analysis device during desorption. Desorption preferably uses rapid heating. Microscale preconcentrators provide advantages regarding thermal cycling and desorption, particularly that heating for accomplishing desorption can be conducted quickly and with low power.

Examples of microscale preconcentrators are disclosed in Manginell et al., U.S. Pat. No. 6,527,835, entitled Chemical Preconcentrator with Integral Thermal Flow Sensor, and in Manginell et al., U.S. Pat. No. 6,171,378, entitled Chemical Preconcentrator.

Example chemical preconcentrators may be formed from a substrate having a suspended membrane, such as low-stress silicon nitride, and incorporate a flow over design. Other successful microscale preconcentrators with a flow through design are disclosed in U.S. Patent Application Publication No. 20050095722 (incorporated by reference herein), published May 5, 2005, and entitled "Microscale Flow Through Sorbent Plate Collection Device", and in U.S. Patent Application Publication No. 20050226778, published Oct. 13, 2005, and entitled "Microscale Flow Through Sorbent Plate Collection Device" (also incorporated by reference herein). The flow through design can increase contact between the analyte fluid flow and the sorbent in the collection area compared to typical flow over designs that would require creating a turbulent flow to match the level of analyte fluid-sorbent contact.

Another example preconcentrator design provided by some of the inventors of the present application is provided in U.S. Patent Application Publication No. 2009/0249958, application Ser. No. 12/337,449, which is incorporated in its entirety by reference herein.

SUMMARY OF THE INVENTION

Embodiments of the present invention provide, among other things, an interchangeable preconcentrator assembly for delivering an analyte to an analysis instrument. The assembly includes a housing defining an inner chamber. An inlet is in fluid communication with the inner chamber, an outlet is in fluid communication with the inner chamber for delivering fluid to the inlet of the analysis instrument, and an exhaust outlet is in fluid communication with the inner chamber. A plurality of removable preconcentrator packages are disposed within the inner chamber. Each of the removable preconcentrator packages including a microscale preconcentrator.

A fluid flow path is defined between the inlet and the inner chamber. A first fluid flow path is defined between the preconcentrators and the exhaust outlet, and a second fluid flow path is defined between the preconcentrators and the outlet. A selectably operable valve directs fluid flow from the inner chamber into either the first fluid flow path or the second fluid flow path.

DETAILED DESCRIPTION

Figure 1:
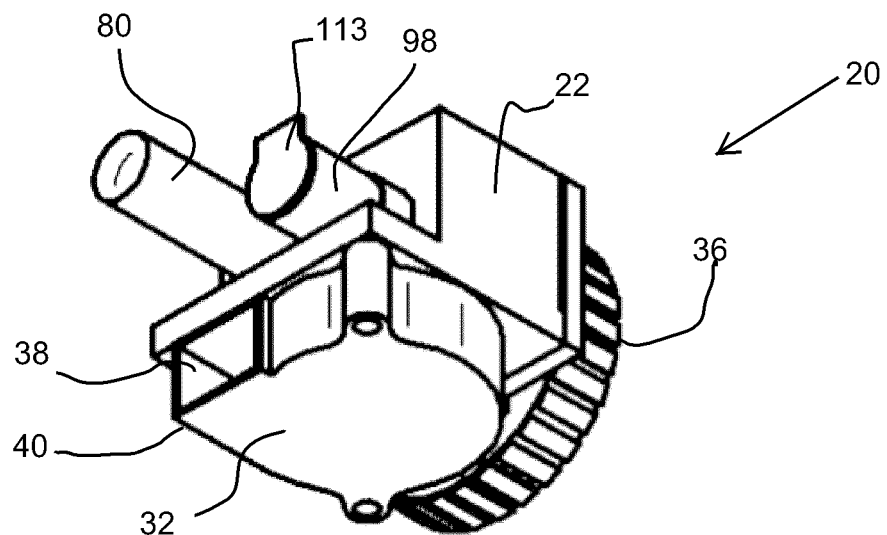
FIG. 1 is a front bottom perspective view of an example preconcentrator assembly according to an embodiment of the present invention.
Figure 2:
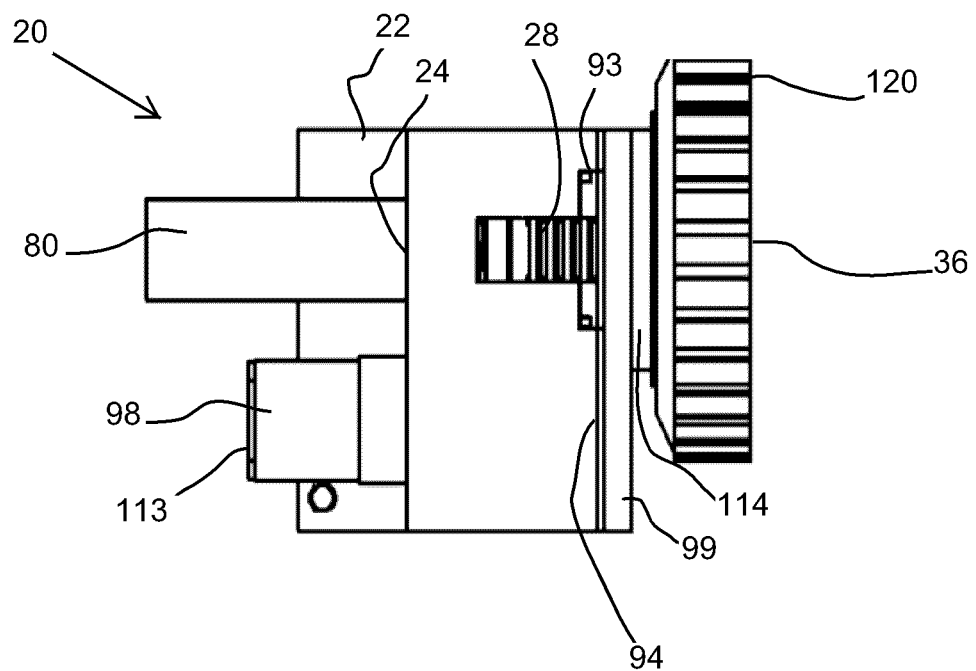
FIG. 2 is a top plan view of the example preconcentrator assembly.
Figure 3:
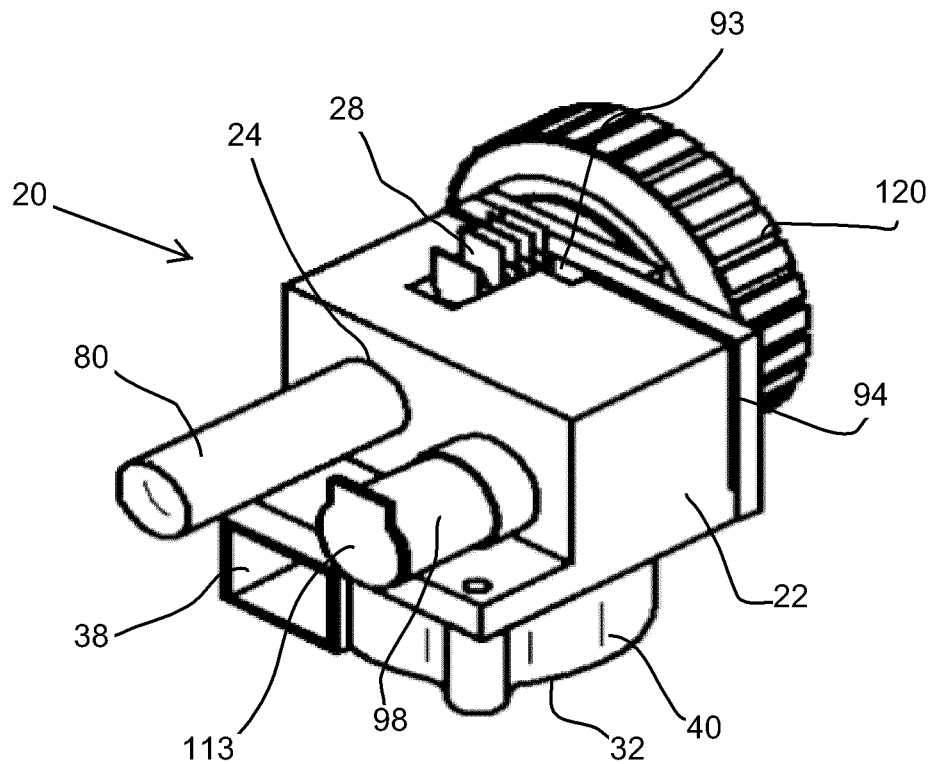
FIG. 3 is a front top perspective view of the example preconcentrator assembly.
Figure 4:
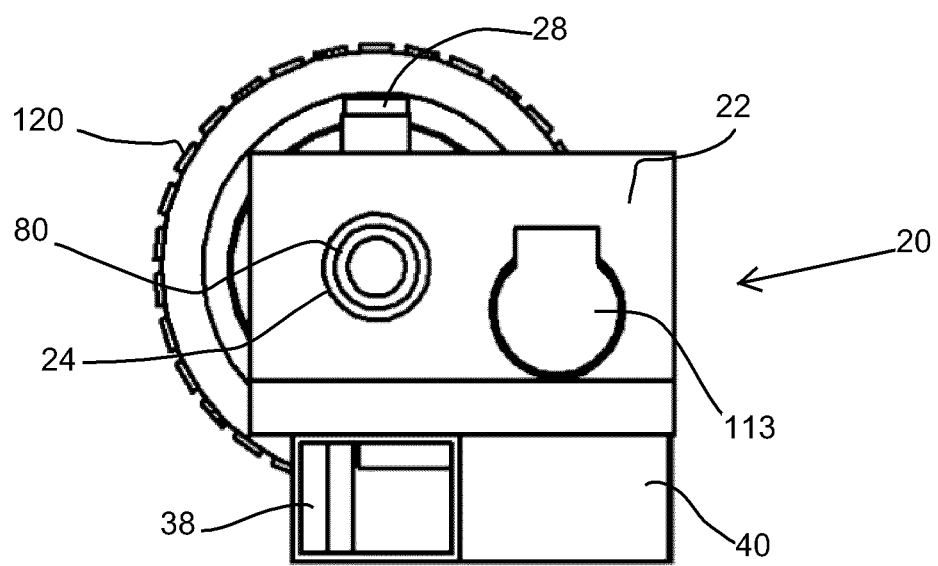
FIG. 4 is a front elevation view of the example preconcentrator assembly.
Figure 5:
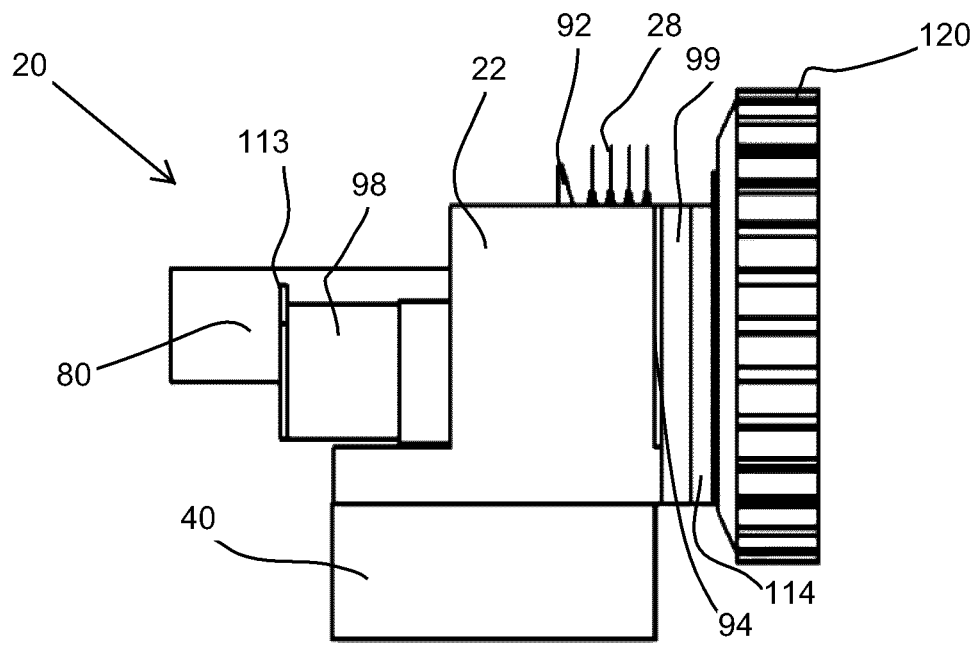
FIG. 5 is a side elevation view of the example preconcentrator assembly.
Figure 6:
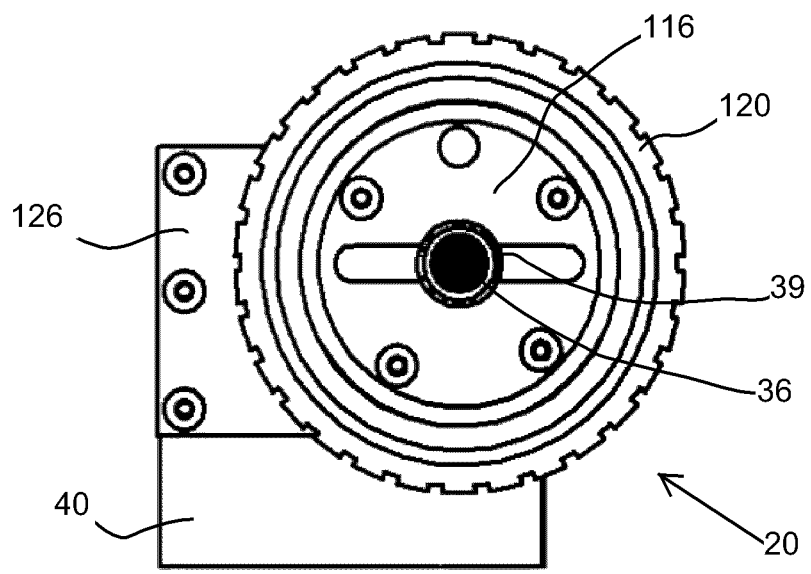
FIG. 6 is a rear elevation view of the example preconcentrator assembly.
Figure 7:
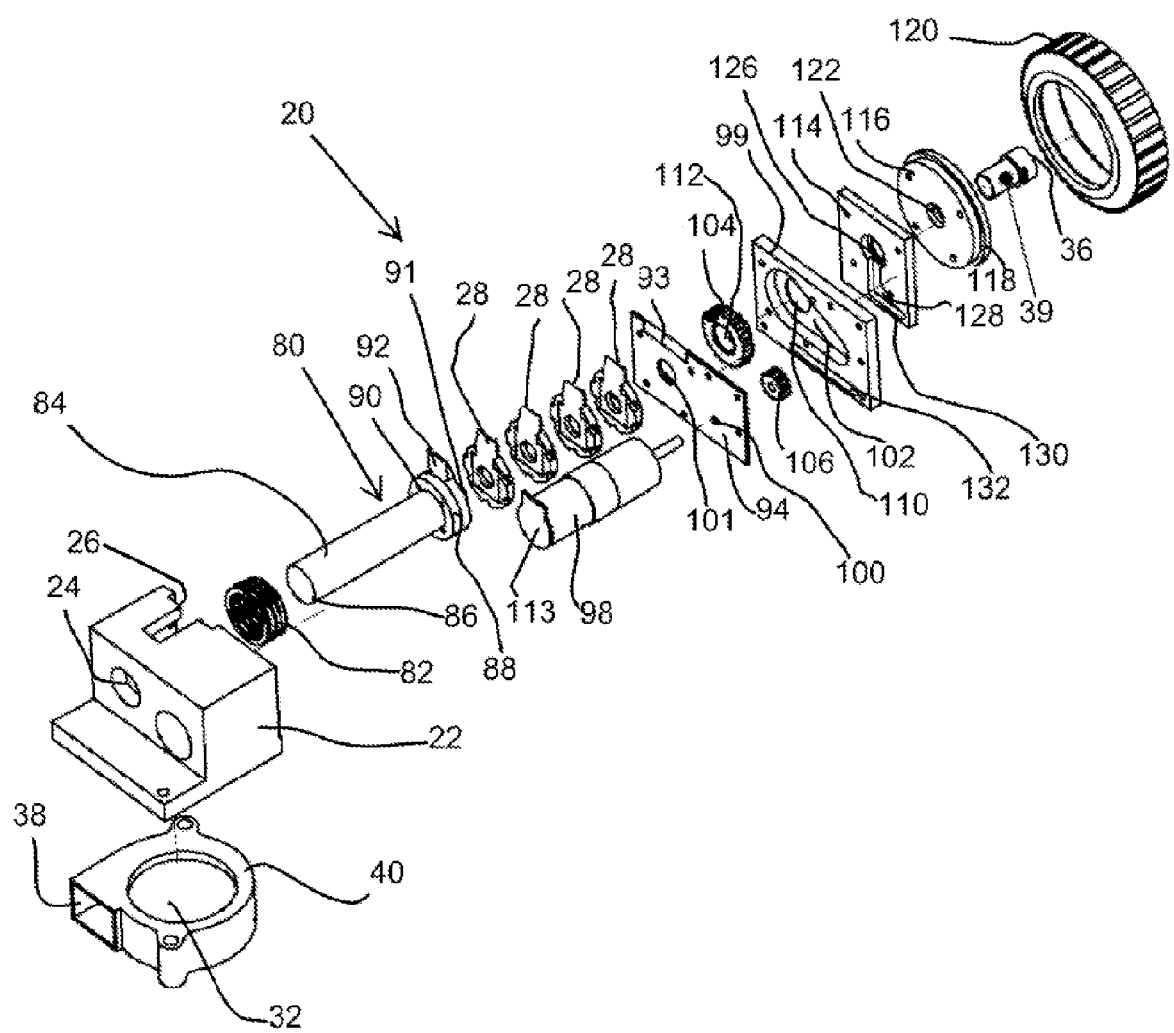
FIG. 7 is an exploded view of an example preconcentrator assembly.
Figure 8:
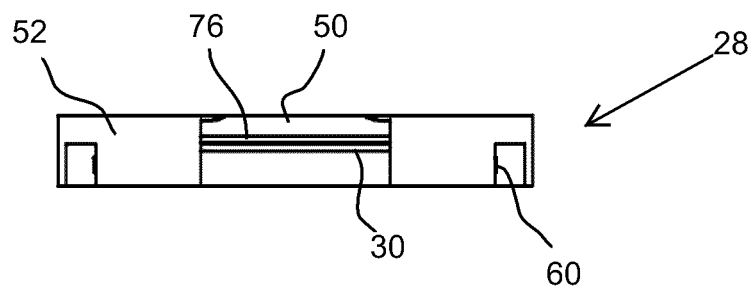
FIG. 8 is a side elevation view of an example analytic preconcentrator package.
Figure 9:
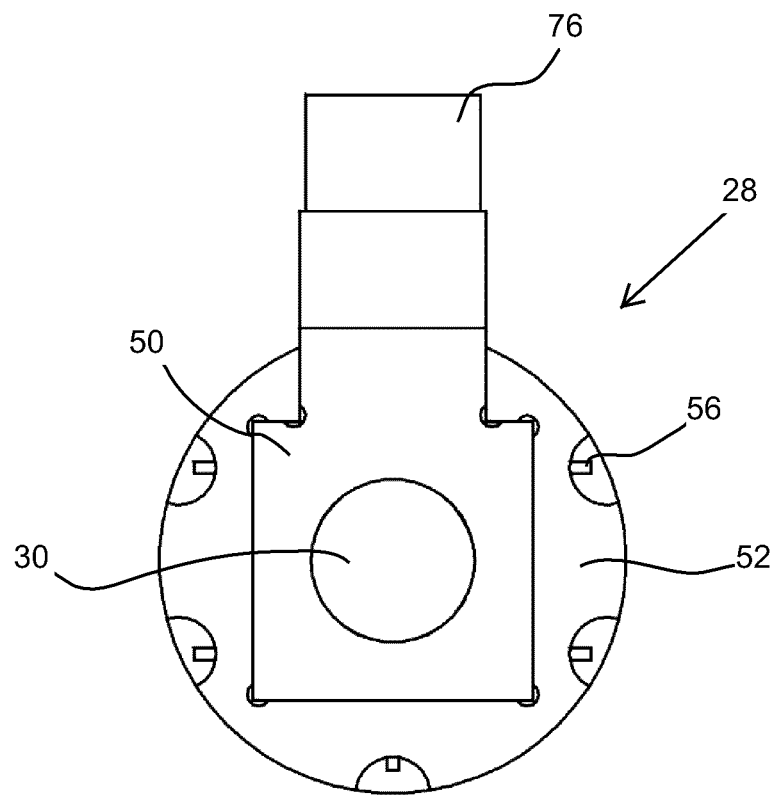
FIG. 9 is a top plan view of the example preconcentrator package.
Figure 10:
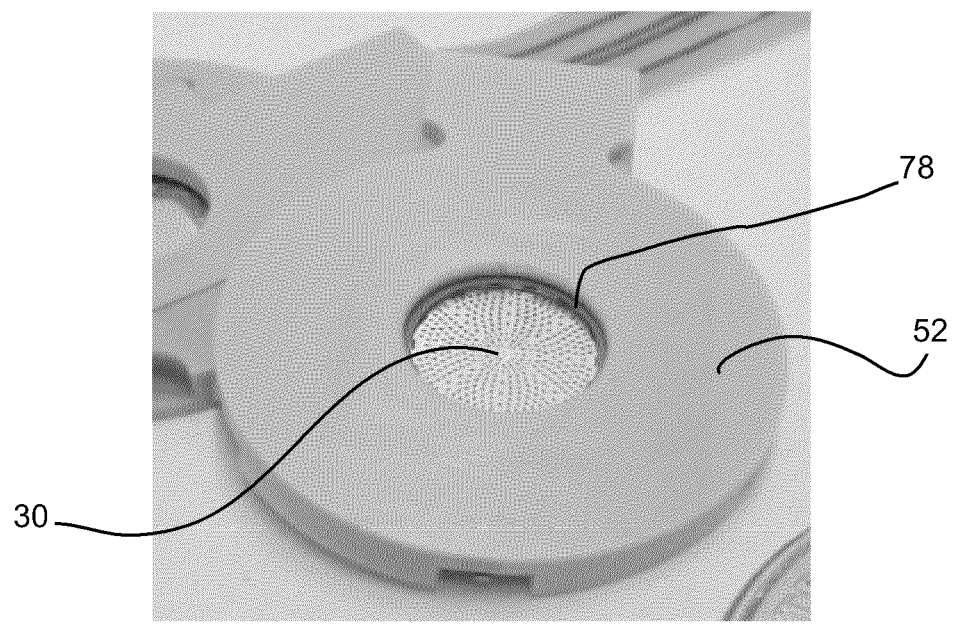
FIG. 10 is a bottom perspective view of the example preconcentrator package, showing a preconcentrator chip therein.
Figure 11:
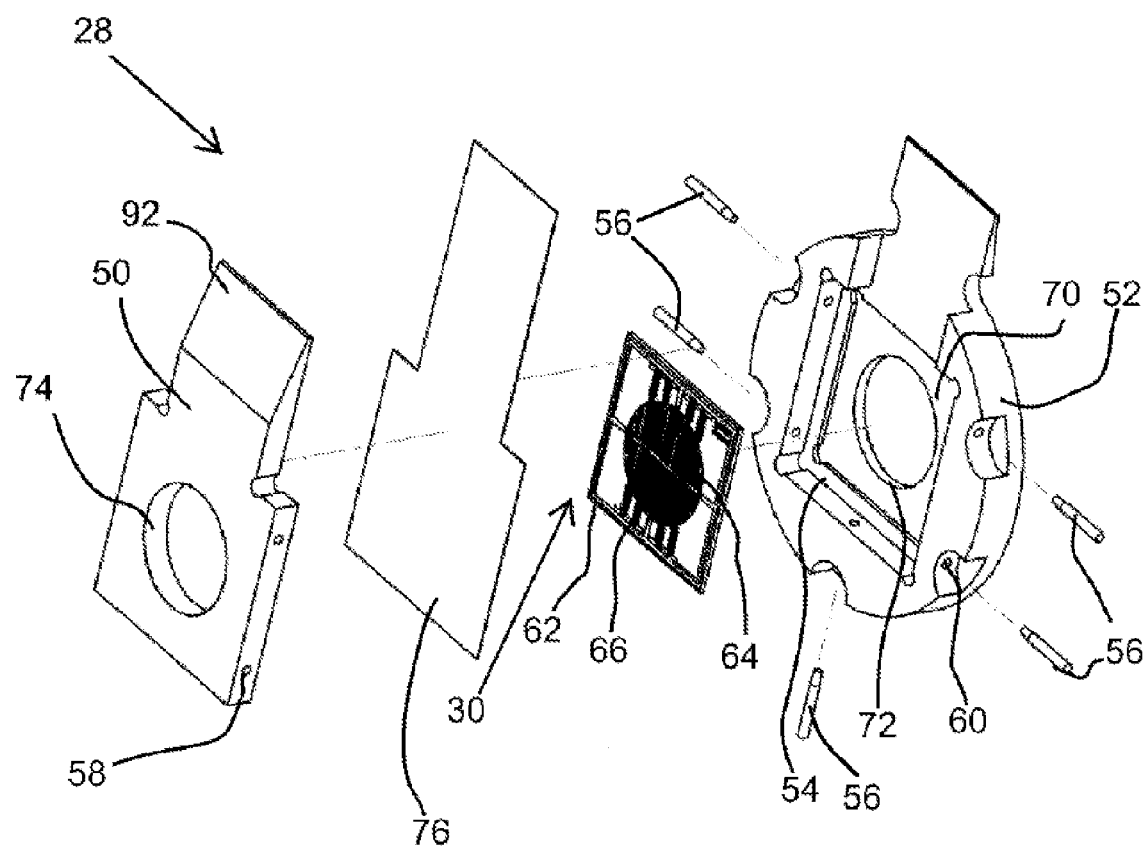
FIG. 11 is an exploded view of an analytic preconcentrator package including the preconcentrator chip.
Figure 12:
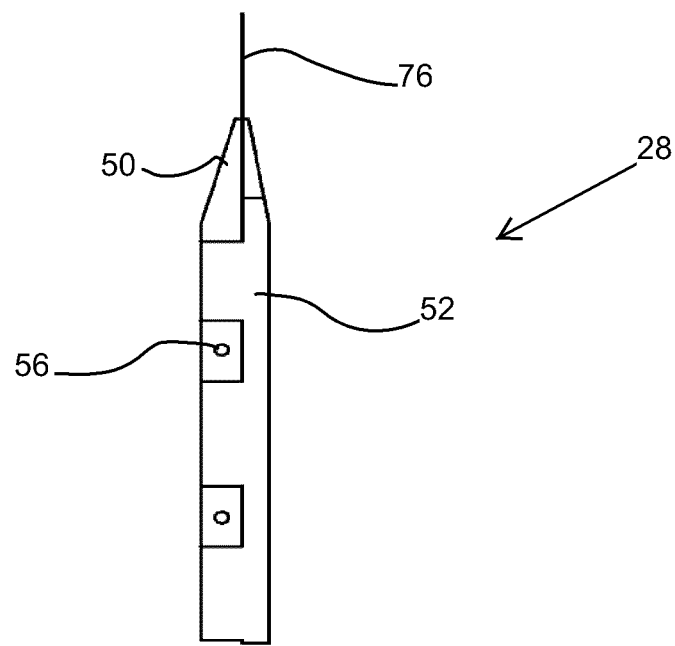
FIG. 12 is a side elevation view of the example preconcentrator package.
Figure 13:
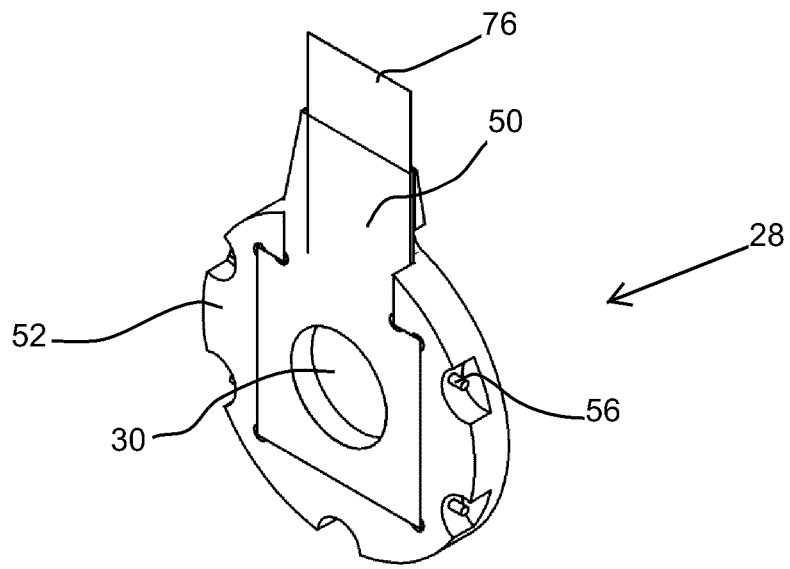
FIG. 13 is a top perspective view of the example preconcentrator package.

Example embodiments of the invention provide, among other things, an interchangeable preconcentrator assembly for connecting to an inlet of an analysis instrument (e.g., an apparatus for analyte storage, analysis, and/or detection). An example assembly permits rapid sequential insertion and removal of a plurality of packaged microscale preconcentrators (preconcentrator packages) into a stacked formation within an inner chamber of a housing to focus or preconcentrate a desired sample or samples of vapors and/or particles, prior to desorption into the analysis instrument. By utilizing this stacked arrangement, a significant increase in sample signal sensitivity can be achieved. Preferred preconcentrator packages hold the preconcentrators in a protective carriage that includes electrodes for connection to a control circuit. Example preconcentrators include a microscale preconcentrator chip having a plurality of through holes and a heater for heating a surface of the chip. The package can include, for example, plates at least partially enclosing the chip, and at least one electrode coupled to the heater and extending between the plates.

The example assembly includes an inlet in fluid communication with the inner chamber, an outlet in fluid communication with the inner chamber for connecting to the inlet of the analysis instrument, and an exhaust outlet in fluid communication with the inner chamber. In this way, a first fluid flow path is defined between the preconcentrators and the exhaust outlet, preferably away from the analysis instrument (if the analysis instrument is coupled to the assembly), and a second fluid flow path is defined between the preconcentrators and the outlet. A valve is provided in example embodiments for selectively directing fluid flow from the inner chamber into either the first fluid flow path or the second fluid flow path. The valve can be controlled by a selectively operable motor in example embodiments. A fluid flow device separate from, coupled to, or even integrated with the assembly can be provided for directing fluid flow into or away from the inner chamber. A fluid flow device (e.g., a low power fan), which in particular example embodiments is disposed in a lower portion of the housing, preferably induces fluid flow that is directed from the inner chamber to the exhaust outlet, which in such examples may also be in the lower portion. In other embodiments, a fluid flow device is alternatively or additionally provided by an external device.

In some example embodiments, an urging member disposed in the assembly pushes against one or more of the inserted preconcentrator(s) packages, which are held within the inner chamber, to align and secure them such that fluid flow will be primarily through the preconcentrators from the inlet to the assembly. This urging member can be biased, such as by a biasing member. In other embodiments, the inserted preconcentrators are held within the housing by components such as magnets, fasteners, quick disconnects, etc.

Example assemblies may be useful, for example, in analyte detection and analysis systems and methods, as might be used for the collection, detection, and analysis of a wide range of vapors or gases, particulate, and liquid-bound analytes. An example assembly of the invention can be configured to attach to or be integrated into one or more analysis instruments, for instance at an opening of a detector. A nonlimiting example detector that may be used is an ion mobility spectrometer (IMS). For example, an assembly can be configured to attach to an IMS or be formed as part of the IMS. However, while example embodiments will be described as configured for an IMS, an assembly of the invention could also be configured to attach, for example, to any suitable analysis instrument, such as but not limited to a gas chromatography column or other instrument.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

FIGS. 1-7 show an assembly 20 for delivering analyte to an inlet of an analysis instrument. The assembly includes a housing 22 having an entrance opening or inlet 24, which provides a fluid path leading to a chamber 26 (see FIG. 7) holding a plurality of arranged (e.g., stacked and aligned, though complete alignment is not necessary) microscale preconcentrator packages 28. The housing block may be substantially hollow to partially or fully define the chamber 26. The chamber 26 in an example embodiment is partially defined by inner walls of the housing 22, though the chamber can be provided by any enclosed (or at least partially enclosed) space that is partially or completely within the housing. The example housing 20, which acts as a thermal insulation layer, encloses the entire arrangement of stacked preconcentrator packages 28 within the chamber 26, allowing a seal to prevent the sample fluid from escaping.

An example assembly 20 accepts a plurality of the packages 22. The number of packages accepted can vary, with a nonlimiting example being five packages, though this number can be lower or higher. Each of the packages 28, best shown in FIGS. 8-13, contains a microscale preconcentrator (micropreconcentrator) 30. Microscale as referred to herein indicates that the micropreconcentrators 30 are, for example, less than 10 mm×10 mm×1 mm in size. A nonlimiting pore area for the micropreconcentrators 30 is about 800 square microns.

Referring again to FIGS. 1-7, a fluid flow inducing device 32, such as but not limited to a fan, and preferably a low power fan, forces sample fluid through the assembly 20 to preferably sustain a constant flow that will not damage the micropreconcentrators 30. Sample fluid may be virtually any fluid, including but not limited to air, and preferably includes one or more analytes (which may be any analyte capable of being concentrated by preconcentrators of the present invention). Though FIGS. 1-7 show the fan 32 being disposed downstream from the micropreconcentrators 30, it is contemplated that a fluid flow inducing device may be disposed either upstream or downstream from the micropreconcentrators, and may be separate from the housing 22. Though the fan 32 is provided in the example assembly 20, it is also contemplated that an external fluid flow inducing device may be used. However, integrating the fan 32 with the housing 22 preferably provides a more complete assembly for use.

During absorption, the sample fluid passes through the inlet 24 and through and/or over the plurality of (unheated) micropreconcentrators 30 in the inner chamber 26, and thus the micropreconcentrators inherently collect desired vapors and/or particles. A fluid flow path is thus defined between the inlet 24 and the micropreconcentrators 30 in the chamber 26.

In the example assembly 20, the inner chamber 26 of the housing 22 is in fluid communication with an outlet 36 at a rear portion of the assembly, so that the outlet can interface with an inlet of an analysis device. Also, the inner chamber 26 is in fluid communication with an exhaust outlet 38 that is preferably directed away (in any direction) from the outlet 36. Thus, a first flow path (FIG. 14) is defined between the inner chamber 26 and the exhaust outlet 38, and a second fluid flow path (FIG. 15) is defined between the inner chamber and the outlet 36. In the example assembly 20, the outlet 36 is provided by a sleeve 39 disposed at a back end of the assembly 20 (e.g., see FIG. 6), and the exhaust outlet 38 is defined by a lower portion 40 of the housing 20, which in an example embodiment also supports the fan 32. This lower portion 40 may be integral with the housing 20 or may be attached to the housing.

Referring now to FIGS. 8-13, to protect the preconcentrator chip 30 and facilitate insertion, alignment, and removal of the example preconcentrator packages 28, the packages include opposed front and back outer plates 50, 52 of Polyetheretherketone (PEEK) material encasing the preconcentrator chip. Though other materials are contemplated, PEEK is preferred as a polymeric material for the package 28 and other components of the assembly 20 due to its very low out-gassing and extremely high chemical and temperature resistance. Other materials may be used that have similar characteristics, however, such as other low thermal conductive material.

The front and back outer plates 50, 52 in an example embodiment engage one another, for instance seated flush with one or another front to back. A sealant, such as a gasket (not shown), may be disposed between the plates 50, 52, engaged at an outer seat 54 of the back outer plate 52, etc., to generally enclose the carriage and protect the microprecentrator chip 30, though this is not required in all embodiments. Alignment pins 56 preferably engage with corresponding openings 58 of the front outer plate 50 and openings 60 of the back outer plate 52 to maintain alignment of the front and back outer plates and fasten the outer plates. Preferably, except for the outer seat 54, the back outer plate 52 is generally disk (e.g., circular or oval) shaped. The front outer plate 50, and accordingly the outer seat 54, is preferably generally rectangular (e.g., square) in shape.

The example individual preconcentrator chips 30 include a substrate 62, e.g., silicon, having a substantially central, circular porous region 64 providing a flow-through area for receiving fluid flow (though in other embodiments, the preconcentrator chips 30 can have a flow-over design, as will be appreciated by artisans). The porous region 64 can be heated by, for instance, resistive heater traces disposed on the substrate 62 (e.g., surrounding and/or over the porous region) that are coupled to an external power source via suitable connections 66 disposed on the substrate. Further, the porous region 64 may be coated with a suitable sorbent coating or coatings for sorbing analyte(s) of interest. Because the packages 28 are preferably easily insertable and removable from the assembly 20, modular packages having preconcentrator chips 30 customized for sorbing analytes of interest can be prefabricated and stored, and later selected for use. Example features of example individual microscale preconcentrator chips are provided in U.S. Patent Application Publication No. 20050095722 (incorporated by reference herein), published May 5, 2005, and entitled "Microscale Flow Through Sorbent Plate Collection Device", though any suitable flow-through or flow-over microscale preconcentrator chip, preferably with a selectively activated heater, may be used.

To further secure the preconcentrator chip 30, an inner seat 70 shaped to match (or at least constrain movement of) the preconcentrator chip substrate 62 may be provided on the back outer plate 52. The inner seat 70 includes an opening 72 (as shown by example in FIGS. 2-3, a circular opening) aligned with at least a portion of the surface of the preconcentrator chip 30 (e.g., the circular porous region 64) for allowing fluid flow from the preconcentrator chip. Similarly, an opening (e.g., a circular opening) 74 is provided in the front outer plate 50, and aligned with the surface of the preconcentrator chip 30 for allowing fluid flow to the preconcentrator chip.

A flex circuit 76, e.g., a polyimide thin film flex board, used for external device powering, is inserted between the front outer plate 50 and the microscale preconcentrator chip 30, and may be bonded to the preconcentrator chip prior to final assembly of the package 28 to enable connection to the integral resistive heater traces on the micropreconcentrator chips. Those of ordinary skill in the art will appreciate that various types of electrical connections can be used. The example flex circuit 76 includes (e.g., printed thereon) one or more electrical couplings (not shown) to the connections 66 coupled to the resistive heaters. Contact electrodes (not shown), for example, can formed on the flex circuit 76 (e.g., printed on a rear side of the flex circuit), extending beyond the front and back outer plates 50, 52, and thus are exposed so that the heating for the absorption and desorption cycles of the micropreconcentrators 30 can be selectively controlled. An opening 78 (not shown in FIG. 11, best seen in FIG. 10), aligned and sized to substantially match the opening 72, 74 of the front and rear outer plates 50, 52, preferably is provided in the flex circuit 76 to allow fluid flow. Instead of or in addition to providing a flex circuit, in other embodiments, suitable electrodes can be provided with (e.g., embedded in, formed in or on) the cartridge housing, such as on the front and/or back outer plates 50, 52.

The example assembly 20 accepts one or more of the modular packages 28, permitting readily the addition and/or removal of the packaged micropreconcentrators 30 into the inner chamber 26 of the housing 22 to reach desired sensitivity levels, and/or to concentrate or exclude particular analytes. Thus, the nature of testing to be conducted can be changed on the fly with a simple change of package(s) 28. Referring again to FIGS. 1-7, to accept and hold the packages in the housing 22, the packages 28 preferably are accepted in the chamber 26 under bias supplied by an urging member such as but not limited to a plunger assembly 80, which in turn is biased by a biasing member, such as but not limited to a spring 82. The example plunger assembly 80 is made of a material having low thermal capacity and low thermal conductivity. An example plunger assembly material is PEEK. The plunger assembly 80 and the spring 82 together provide biasing via spring loading for maintaining position of the preconcentrator packages 28.

A hollow tube portion 84 of the plunger assembly 80, which preferably is disposed in the inlet 24 of the housing 22, includes an opening 86 completely there through to provide an inlet for a fluid flow path through the housing 22, including through and/or over the micropreconcentrators 30. However, it is also contemplated that the fluid flow path may be around or adjacent to the urging member in other embodiments, and in this case a substantially hollow tube portion may not be necessary. Also, if the packages 28 are attached to the housing 22 (e.g., to the inlet 24 or other parts of the housing), the biasing member (e.g., spring 82) may be omitted.

In an example embodiment, the plunger assembly 80 further includes a head 88 at one end of the tube 84. The head 88, which may be formed integrally with or coupled to the tube 84, includes a front surface 90 for contacting and longitudinally constraining the biasing member 82, and an engaging surface 91 for engaging one of the micropreconcentrator packages 28. An extension 92 is preferably provided either as an integral part of or a separate part connected to the head 88 for supporting the contact electrodes of the flex circuit 76 when the assembly 20 is completed. The extension 92 and the upper portions of the packages 28 are disposed in a longitudinal opening of the housing 22 when the packages are loaded.

The urging member 80 in the example assembly 20 is biased against the packages 28 to accept them, hold them, and permit removal, while also limiting flow to be primarily through and/or over the micropreconcentrators 30. Other ways to allow the packages 28 to be accepted, held, and selectively removed, such as but not limited to, fasteners, magnets, etc., may be used in place of or in addition to the urging member 80 and biasing member 82.

After the housing 22 is assembled, the modular packages 28 can be sequentially dispensed into the housing, preferably using a loading tool, such as but not limited to a pair of tweezers/forceps. The loading tool(s) may be configured as needed considering the packages 28, housing 22, and/or operating environment. The preconcentrator packages 28 preferably are sequentially dispensed into the assembled housing 22 by using the loading tool to slide the disk between the biased (e.g., spring loaded) plunger assembly 80 and a lead-in 93 which preferably is machined into a front plate 94 of a valve housing. In other embodiments, the packages 28 can be connected to one another and/or the housing 20 in different ways, such as connectors, co-forming, magnets, etc.

For selectively controlling fluid flow from the micropreconcentrators 30 to the analysis instrument; that is, to either the first fluid flow path or the second fluid flow path described above, a valve is provided. In the example assembly, the valve is a sleeve valve. An example sleeve valve significantly reduces the overall dimension of not only the assembly 20 but the region between the micropreconcentrators 30 and the inlet of any attached analysis instrument, reducing the volume and the signal attenuation while also permitting an increase in flow without increasing the pressure drop across the orifice.

In the example sleeve valve arrangement, the desorption sleeve 39 is provided, which is made of a material having low thermal capacity and high thermal conductivity. The example desorption sleeve 39 primarily scavenges heat from the analysis instrument, with its low thermal mass, and maintains the same temperature as the analysis instrument, preventing any sample vapors and/or particles from attaching/condensing to the exposed sleeve areas during collection or detection.

In a nonlimiting example embodiment, the sleeve valve is driven by a low power (DC) stepper motor 98, which controllably rotates the valve by a small belt and pulley system. To close the housing 22 and support the sleeve valve, the rear of the housing may be provided partially by a valve housing block that includes the front plate 94 and a rear plate 99. Thus, in an example assembly 20, the front plate 94 (of the valve housing), with the housing block 20, helps generally define the chamber 26. Other types of actuation are possible for driving the valve.

The front plate 94 preferably includes an opening 100 for accepting the shaft of the low power stepper motor, and further includes a throughhole 101 for providing a fluid flow path from the micropreconcentrators. Fixedly connected to and adjacent to the front plate 94, the back plate 99 of the valve housing block includes a seat 102 for accepting a sleeve valve 104 and a wheel 106 of the stepper motor 98. The wheel 106 is coupled to the sleeve valve 104 such as via a belt, or by other forms of mechanical actuation such as (but not limited to) gears, etc., for opening and closing the sleeve valve. Thus, in an example embodiment, the seat 102 generally can accept a pulley for controlling the sleeve valve 104 via the motor 98. A portion of the seat 102 includes a throughhole 110 aligned with an opening 112 of the sleeve valve 104 and aligned with the throughhole 101 in the front plate 94 of the valve housing block. Additional through holes may be provided in the front and back plates 94, 99 for accepting fasteners used to fixedly assemble the valve housing block.

In an example embodiment, the motor 98 is coupled to a suitable controller and supply source, for example connected via a printed circuit board (e.g., drive board) 113, and/or coupled to a power supply (or may be operated by an internal battery). In some example embodiments, the motor 98 may be attached to the printed circuit board, though not in all embodiments. In some example embodiments, the board and other suitable controller components and the power supply are attached to the assembly 20, to a larger unit (such as a handheld unit including the assembly and the analysis instrument), or elsewhere. Those of ordinary skill in the art will appreciate that various devices and methods for powering and controlling the motor 98 are possible.

In the example assembly 20, to help connect the assembly to an analysis instrument and define fluid flow channels from the micropreconcentrators 30, a rear plate 114 is connected to the back plate 99 of the valve housing block. This rear plate 114 is in turn attached to a circular plate 116 having an outer flange 118 that engages an inner surface of a threaded ring 120 to hold the threaded ring between the rear plate 114 and the circular plate 116. The threaded ring 120 includes threads for connecting the assembly to an inlet of an analysis instrument. It will be appreciated that the threaded ring 120 can vary depending on the analysis instrument to be attached thereto. The circular plate 116 seals the entrance to the analysis instrument from the micropreconcentrators 30 except for the opening 122 through which the desorption sleeve 39 passes. Thus, the desorption sleeve 39 and sleeve valve 104 can be selectively operated via the motor 98 to open and close fluid flow to the analysis instrument, directing fluid flow either to the analysis instrument (along the second fluid flow path shown in FIG. 15) or away from the analysis instrument (along the first fluid flow path shown in FIG. 14). In other embodiments, the plate 116 is not circular, though a circular plate is useful for fitting to particular systems. FIG. 16 shows the assembly 20 attached to an analysis instrument 125. The example preconcentrator assembly 20 and preconcentrator packages may be used with existing or to-be-known analysis instruments, including but not limited to IMS detectors, to improve sensitivity of the analysis instruments.

The rear plate 114 includes a throughhole 126 aligned with the throughhole of the valve housing (and thus in the overall fluid flow path through and/or over the micropreconcentrators). Additionally, the rear plate 114 includes a seat 128, which defines a chamber when the rear plate is flush with the back plate 99 of the valve housing, to direct fluid flow away from the preconcentrators (that is, along the first fluid flow path shown in FIG. 14, and away from the analysis instrument). In a nonlimiting example embodiment, this chamber leads from the throughhole 126 in the rear plate 114 to an elongated portion 130 aligned with an elongated throughhole 132 in the back plate of the valve housing. A fluid flow path is thus provided from the seat 128 of the rear plate 114 to a lower chamber at a bottom of the housing 20, and to the exhaust outlet 38 for egress of the fluid. This lower chamber can be defined by, for instance, the lower housing portion 40 attached to the housing 20, though in other embodiments it can be defined by an integral part of the housing.

Referring again to FIGS. 14-15, the fluid will first travel through the inlet 24 of the assembly 20 through the plunger assembly 80. The housing block 22, which acts as a thermal insulation layer, encloses the stacked preconcentrator packages 28 in the chamber 26, allowing a seal and preventing the sample fluid from escaping. The fluid exits the inner chamber 26, passing through the front plate 94 of the valve housing block and to the sleeve valve 104 and sleeve 39. Depending on the selective operation of the sleeve valve 104 and sleeve 39 via the motor 98, the fluid is then directed to either the lower chamber in the lower housing portion 40, preferably with the fluid flow inducing device 32 on, or the fluid/air enters the analysis instrument via the sleeve 39 (and with the fluid flow inducing device preferably off).

Figure 14:
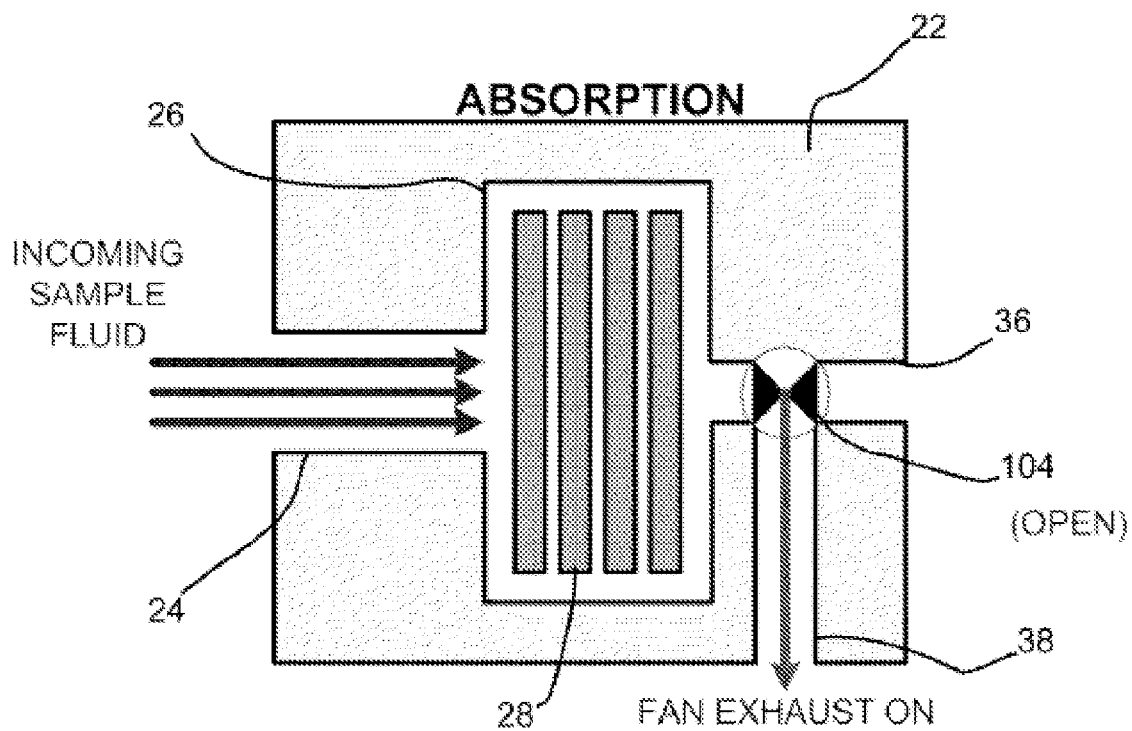
FIG. 14 shows sample absorption onto example analytical preconcentrators according to embodiments of the present invention.

During absorption, as shown in FIG. 14, the fluid flow inducing device 32, preferably disposed downstream from the packaged micropreconcentrators 30 forces fluid through the system, sustaining a constant flow that will not damage the analytical preconcentrators 30. A selectable opening, such as but not limited to a valve in the analysis instrument, is closed, and the sleeve valve 104 within the housing 20 is open, permitting the fluid to egress the housing via the second flow path and toward the exhaust outlet 38, so that it can be used at the fan exit, potentially releasing other chemical/explosive particles from a surface. Sample fluid thus passes through and/or over the stack of unheated analytical preconcentrators, inherently collecting desired vapors and/or particles.

Figure 15:
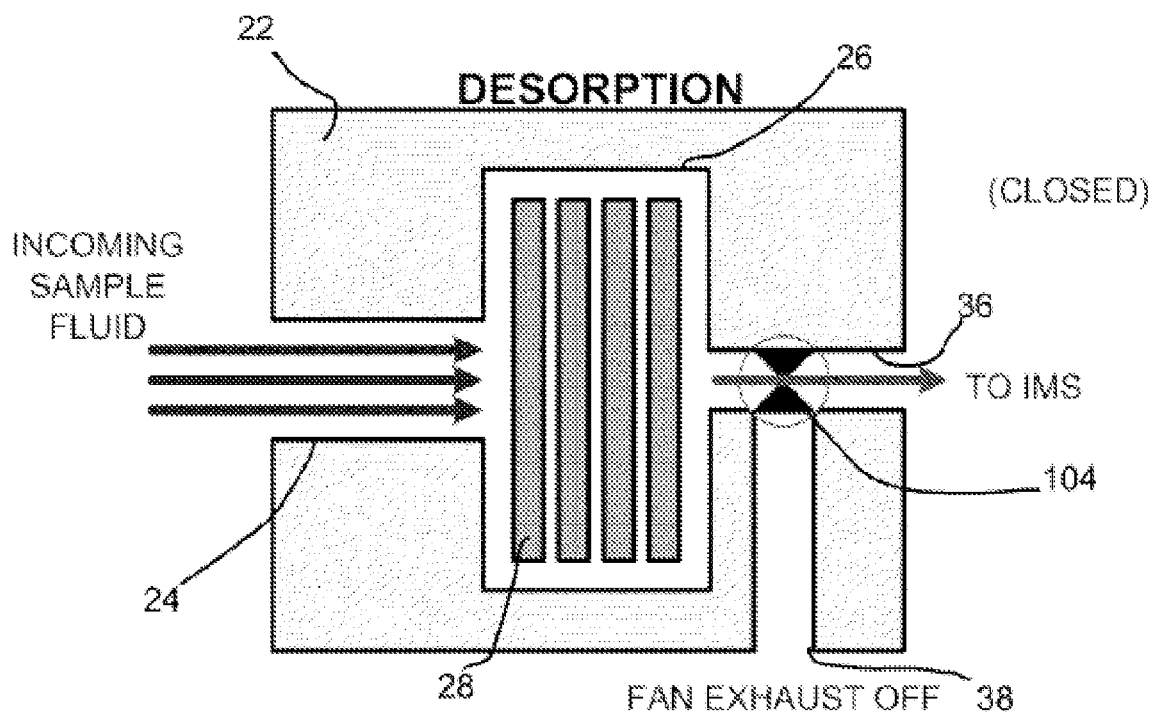
FIG. 15 shows sample desorption off of analytical preconcentrators to an analysis instrument.
Figure 16:
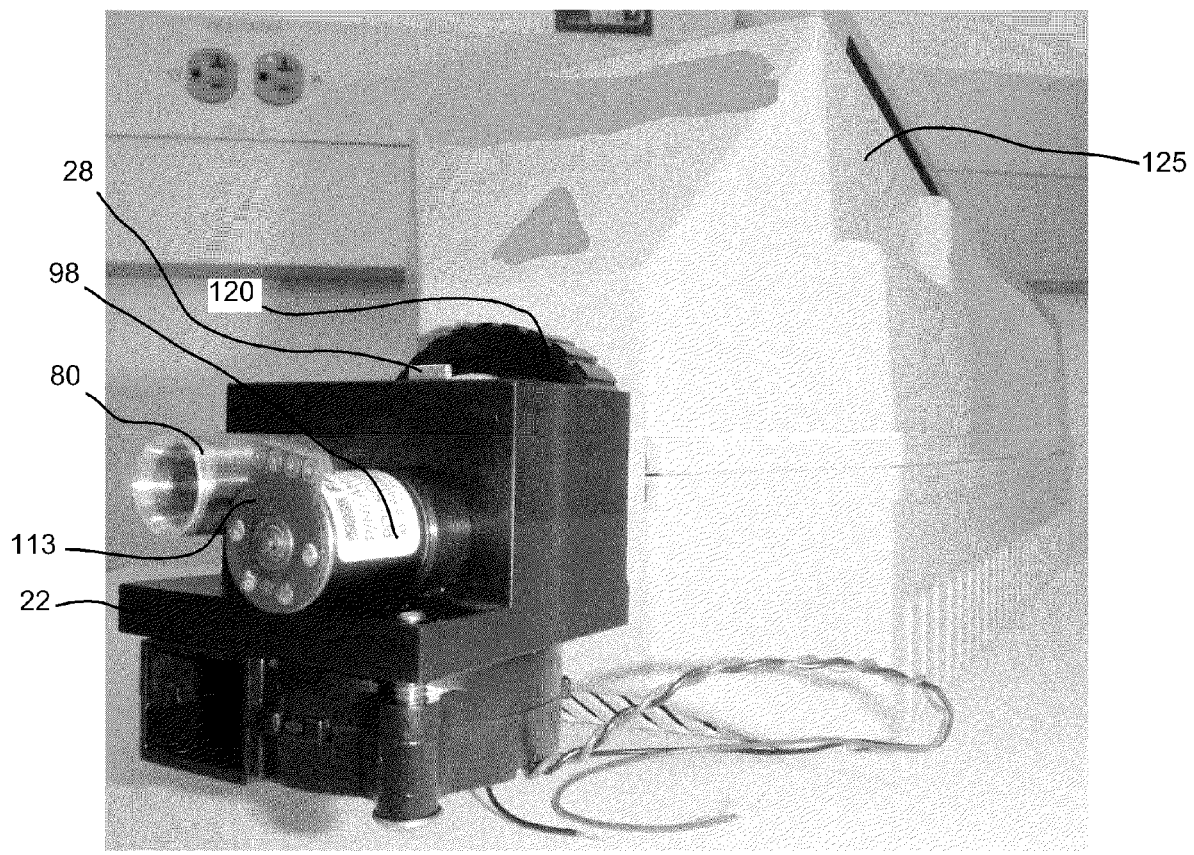
FIG. 16 shows an example preconcentrator assembly mounted to an analysis instrument.

Referring to FIG. 15, during desorption mode, sample fluid continues to pass through the stack of (now heated) analytical preconcentrators 30, inherently desorbing the desired vapors and/or particles. The sleeve valve 104 is closed, and the internal analysis instrument (e.g., IMS) valve is open, permitting the fluid to enter the IMS through the short, low volume desorption sleeve 39 and through the outlet 36 for detection.

Embodiments of the present invention can preconcentrate a detection sample at the inlet of a detection device at the microscale or chip level. Further, preferred preconcentrator assemblies can mount directly to a detection unit and are completely modular. Example assemblies can be employed for existing analysis instruments (e.g., IMS detectors) and future instruments, to improve sensitivity. Various chip sizes and types can be used in an example arrangement to stack and thus potentially increase signal sensitivity. Potential sample signal sensitivity can be significantly increased compared to some conventional systems.

Additionally, the example desorption sleeve scavenges heat from the analysis instrument with its low thermal mass, and it maintains the same temperature as the analysis instrument, preventing any sample vapors and/or particles from attaching or condensing to the exposed sleeve areas during collection/detection. This example sleeve valve arrangement significantly reduces the overall dimension of not only the module assembly but the region between the micropreconcentrators and the inlet of the analysis instrument, inherently reducing the volume and the attenuation of the signal, while also permitting an increase in flow without increasing the pressure drop across the orifice. The provided fluid flow inducing device 32 or a secondary device can be used to expel chemical/explosive particles off of various surfaces to enhance collection efficiencies.

The example preconcentrator assembly 20 can be implemented, as nonlimiting examples, as a module that focuses explosive particles and inherently explosive vapors at the inlet of an explosive detection system, which is retrofitted to an existing heating, ventilating, and air conditioning (HVAC) system, such as an HVAC system in a place of public use (e.g., shopping malls, sporting arenas, amphitheaters, museums, and many others). Explosive particles and inherently explosive vapors can be detected at the inlet of an explosive detection system that is placed inside a cargo/shipping/in-flight container. Other implementations include inside waste disposal containers for the detection of potential explosive devices in or on public streets. Example modules can focus particles in slow flow of liquid, e.g., drinking water, to detect heavy metals and/or other harmful compounds. Potential applications include, but are not limited to, explosive, narcotics, chemical, heavy metal, and biological detection to increase sensitivity of a detected sample signal.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An interchangeable preconcentrator assembly for delivering an analyte to an inlet of an analysis instrument comprising:
   a housing defining an inner chamber;
   an inlet in fluid communication with the inner chamber;
   an outlet in fluid communication with the inner chamber for delivering fluid to the analysis instrument;
   an exhaust outlet in fluid communication with the inner chamber;
   a plurality of removable preconcentrator packages disposed within the inner chamber, each of said removable preconcentrator packages including a microscale preconcentrator, wherein a fluid flow path is defined between the inlet and the inner chamber;
   the assembly further defining a first fluid flow path between the preconcentrators and said exhaust outlet and a second fluid flow path between the preconcentrators and said outlet; and
   a selectably operable valve for selectively directing fluid flow from the inner chamber into either the first fluid flow path or the second fluid flow path;
   wherein said plurality of removable preconcentrator packages are urged against a surface of said housing by a mechanically biased urging member.

2. The assembly of claim 1, wherein the fluid flow path to the chamber is also defined through said biased urging member.

3. The assembly of claim 2, wherein said mechanically biased urging member comprises:

a plunger including an at least partially open tube defining a space, said plunger including an engaging surface adjacent to said space.

4. The assembly of claim 3, further comprising:
a biasing member for mechanically biasing said mechanically biased urging member toward the surface of said inner housing.

5. The assembly of claim 4, wherein said biasing member comprises a spring.

6. The assembly of claim 1,
wherein the preconcentrator comprises a microscale preconcentrator chip including a substrate having a surface and a heater for heating the surface;
wherein each of said preconcentrator packages further comprises:
first and second plates at least partially enclosing said chip, said first plate having an opening aligned longitudinally with the surface of the preconcentrator chip for allowing fluid flow to said preconcentrator chip; and
at least one electrode coupled to said heater and extending beyond said first and second plates.

7. The assembly of claim 6, wherein each of said at least one preconcentrator package further comprises:
a flex circuit having said at least one electrode provided thereon and coupled to said heater.

8. The assembly of claim 1, wherein said selectively operable valve comprises a sleeve valve and a sleeve.

9. The assembly of claim 8, further comprising:
a motor for selectively operating said valve.

10. The assembly of claim 9, wherein said motor comprises a stepper motor, and wherein said housing includes a portion for accommodating said stepper motor.

11. The assembly of claim 10, wherein said housing further comprises a valve housing block, said valve housing block comprising a plate having a seat for accommodating said sleeve, a wheel of said stepper motor, and a coupling between said sleeve and said stepper motor.

12. The assembly of claim 8, further comprising:
a fluid flow inducing device in fluid communication with the exhaust outlet.

13. The assembly of claim 12, wherein said fluid flow inducing device comprises a low power fan.

14. The assembly of claim 13, wherein the low power fan is disposed within a shroud.

15. The assembly of claim 12
wherein said fluid flow inducing device is disposed within a lower housing portion of said housing;
wherein said lower housing portion includes said exhaust outlet for fluid egress from said housing.

16. The assembly of claim 1, wherein the analysis instrument comprises a detector.

17. The assembly of claim 16, wherein the detector comprises an ion mobility spectrometer (IMS).

18. An interchangeable preconcentrator assembly for delivering analyte to an analysis instrument comprising:
housing means for defining a chamber, an inlet to the chamber, a first fluid flow path leading away from the analysis instrument, and a second fluid flow path leading to the analysis instrument;
means for accommodating at least one preconcentrator chip disposed within chamber;
means for selectively directing fluid flow from the chamber to either the first fluid flow path or the second fluid flow path; and
means for mechanically biasing said at least one preconcentrator chip toward a surface of said housing means;
wherein said means for accommodating comprise first and second plates at least partially enclosing said chip, said first plate having an opening for allowing fluid flow to said preconcentrator chip.

19. A method for preconcentrating an analyte in fluid/air and selectively delivering the preconcentrated analyte to an analysis instrument, the method comprising:
delivering the fluid/air containing the analyte to a plurality of micropreconcentrators disposed within an inner chamber defined by a housing and urged against a surface of said housing by a mechanically biased urging member, while a valve seals the inner chamber from a second fluid flow path in the housing leading to the analysis instrument to permit a first fluid flow path from the inner chamber away from the analysis instrument;
heating the micropreconcentrators; and
selectively operating the valve to permit the first fluid flow path and close the second fluid flow path.

20. The method of claim 19, further comprising:
during said delivering, actuating a fluid flow inducing device disposed within said first fluid flow path.

* * * * *